(12) United States Patent
Mehrpouyan et al.

(10) Patent No.: US 7,781,227 B2
(45) Date of Patent: Aug. 24, 2010

(54) MULTIPLEX MICROPARTICLE SYSTEM

(75) Inventors: Majid Mehrpouyan, Gilroy, CA (US); Diether J. Recktenwald, San Jose, CA (US); Rudolf Varro, Mountain View, CA (US)

(73) Assignee: Becton, Dickinson and Company, Franklin Lakes, NY (US)

( * ) Notice: Subject to any disclaimer, the term of this patent is extended or adjusted under 35 U.S.C. 154(b) by 0 days.

(21) Appl. No.: 12/398,119

(22) Filed: Mar. 4, 2009

(65) Prior Publication Data

US 2009/0163378 A1 Jun. 25, 2009

Related U.S. Application Data

(62) Division of application No. 11/404,348, filed on Apr. 14, 2006, now Pat. No. 7,507,588.

(60) Provisional application No. 60/673,471, filed on Apr. 20, 2005.

(51) Int. Cl.
*G01N 33/543* (2006.01)
*G01N 33/53* (2006.01)

(52) U.S. Cl. ............... 436/523; 435/7.1; 435/287.2; 435/973; 436/518; 436/524; 436/528; 436/546; 436/10; 436/164; 436/172; 422/82.08

(58) Field of Classification Search ............ 435/4, 435/6, 7.1, 7.2, 287.2, 973; 436/517, 518, 436/523–535, 546, 10, 15, 44, 46, 164, 172; 422/82.08

See application file for complete search history.

(56) References Cited

U.S. PATENT DOCUMENTS 4,342,739 A 8/1982 Kakimi et al.
4,717,655 A 1/1988 Fulwyler et al.
5,073,498 A 12/1991 Schwartz et al.
5,326,692 A 7/1994 Brinkley et al.
5,369,036 A 11/1994 Mercolino et al.

(Continued)

FOREIGN PATENT DOCUMENTS

CA 1 248 873 * 1/1989

(Continued)

OTHER PUBLICATIONS

Chen Roy et al: "Simultaneous quantification of six human cytokines in a single sample using microparticles-based flow cytometric technology" Sep. 1999, Clinical Chemistry, vol. 45, Nr. 9, pp. 1693-1695, Oak Ridge Conference, San Jose, California, USA.

(Continued)

*Primary Examiner*—Gailene R Gabel
(74) *Attorney, Agent, or Firm*—Douglas A. Petry

(57) ABSTRACT

Arrays of microparticle populations, each population labeled with a single fluorescent dye, are provided for use in multiplex assays. The populations form a virtual multidimensional array wherein each microparticle is identified by fluorescence intensity in two different fluorescence detection channels. The arrays are useful in a variety of assays, including multiplex, multi-analyte assays for the simultaneous detection of two or more analytes by, for example, flow cytometry, and a labeling reagents in, for example, microscopy. The use of singly-dyed microparticles to form multidimensional arrays greatly simplifies the creation of multiplex assays.

8 Claims, 3 Drawing Sheets

U.S. PATENT DOCUMENTS

| | | | |
|---|---|---|---|
| 5,716,855 | A | 2/1998 | Lerner et al. |
| 5,981,180 | A | 11/1999 | Chandler et al. |
| 6,023,540 | A | 2/2000 | Walt et al. |
| 6,268,222 | B1 | 7/2001 | Chandler et al. |
| 6,514,295 | B1 | 2/2003 | Chandler et al. |
| 6,524,793 | B1 | 2/2003 | Chandler et al. |
| 6,528,165 | B2 | 3/2003 | Chandler et al. |
| 6,592,822 | B1 | 7/2003 | Chandler |
| 6,642,062 | B2 | 11/2003 | Kauvar et al. |
| 6,680,211 | B2 * | 1/2004 | Barbera-Guillem et al. . 436/533 |

FOREIGN PATENT DOCUMENTS

| | | | |
|---|---|---|---|
| EP | 0 296 136 A | 12/1988 | |
| GB | 1 561 042 | 2/1980 | |

OTHER PUBLICATIONS

Fulton, Jerrold et al., "Advanced multiplex analysis with the FlowMetrixTM system," Clinical Chemistry, vol. 43 (9): 1749-1756 (1997).

Cook, E. B. et al., "Simultaneous measurement of six cytokines in a single sample of human tears using microparticle-based flow cytometry: allergics vs. non-allergics." Journ Journal of Immunology Methods 254: 109-118 (2001).

* cited by examiner

MULTIPLEX MICROPARTICLE SYSTEM

CROSS REFERENCE TO RELATED APPLICATIONS

This application is a divisional application of U.S. patent application Ser. No. 11/404,348, filed Apr. 14, 2006, which issued as U.S. Pat. No. 7,507,588 on Mar. 24, 2009, and which claims priority to U.S. provisional application No. 60/673,471, filed Apr. 20, 2005; the disclosures of both of which are incorporated herein by reference.

BACKGROUND OF THE INVENTION

1. Field of the Invention

The present invention relates to arrays of labeled microparticles. Such arrays are particularly useful in multiplex assays, such as biological detection assays and, more particularly, in the fields of flow cytometry and fluorescence microscopy.

2. Description of Related Art

Flow cytometers are well known analytical tools that enable the characterization of particles on the basis of light scatter and particle fluorescence. In a flow cytometer, particles are individually analyzed by exposing each particle to an excitation light, typically one or more lasers, and the light scattering and fluorescence properties of the particles are measured. Particles, such as molecules, analyte-bound beads, individual cells, or subcomponents thereof, typically are labeled with one or more spectrally distinct fluorescent dyes, and detection is carried out using a multiplicity of photodetectors, one for each distinct dye to be detected. Flow cytometers are commercially available from, for example, BD Biosciences (San Jose, Calif.).

Early in the development of flow cytometry, it was recognized that various types of ligand binding assays could be carried out using microparticles (beads) coated with one member of a binding pair. For example, immunoassays can be carried out in a sandwich hybridization assay format using beads coated with an analyte-specific binding agent, such as a monoclonal antibody (mAb), as a capture reagent, and a second analyte-specific binding agent, again typically a mAb, labeled with a fluorophore as a reporter reagent. The coated beads and reporters are incubated with a sample containing (or suspected of containing) the analyte of interest to allow for the formation of bead-analyte-reporter complexes. Analysis by flow cytometry enables both detecting the presence of bead-analyte-reporter complexes and simultaneously measuring the amount of reporter fluorescence associated with the complex as a quantitative measure of the analyte present in the sample.

It was also recognized early in the development of flow cytometry that the simultaneous analysis of multiple analytes in a sample could be carried out using a set of distinguishable beads, each type of bead coated with a unique analyte-specific binding agent. The bead set and fluorescently labeled reporter reagents, one for each species of analyte to be detected, are incubated with a sample containing the analytes of interest to Is allow for the formation of bead-analyte-reporter complexes for each analyte present, and the resulting complexes are analyzed by flow cytometry to identify and, optionally, quantify the analytes present in the sample. Because the identity of the analyte bound to the complex is indicated by the identity of the bead, multiple analytes can be simultaneously detected using the same fluorophore for all reporter reagents. A number of methods of making and using sets of distinguishable microparticles have been described in the literature.

UK Patent No. 1 561 042, published Feb. 13, 1980, and Fulwyler and McHugh, 1990, Methods in Cell Biology 33:613-629, describe the use of multiple microparticles distinguished by size, wherein each size microparticle is coated with a different target-specific antibody.

Tripatzis, European Patent No. 0 126,450, published Nov. 28, 1984 (see also corresponding Canadian Patent 1 248 873), describes multi-dimensional arrays of microparticles formed by labeling microparticles with two or more fluorescent dyes at varying concentrations. Microparticles in the array are uniquely identified by the levels of fluorescence dyes. Tripatzis describes the use of such arrays for the simultaneous detection a large numbers of analytes in a sample by flow cytometry, and, further, describes their use as labels in microscopy.

U.S. Pat. Nos. 4,499,052 and 4,717,655, Entitled: "Method and Apparatus for Distinguishing Multiple Subpopulations of Cells", issued Feb. 12, 1985, and Jan. 5, 1988, respectively, describe the use of microparticles distinguishably labeled with two different dyes, wherein the microparticles are identified by separately measuring the fluorescence intensity of each of the dyes.

Both one-dimensional and two-dimensional arrays for the simultaneous analysis of multiple analytes by flow cytometry are available commercially. Examples of one-dimensional arrays of singly dyed beads distinguishable by the level of fluorescence intensity include the BD™ Cytometric Bead Array (CBA) (BD Biosciences, San Jose, Calif.) and Cyto-Plex™ Flow Cytometry microspheres (Duke Scientific, Palo Alto, Calif.). An example of a two-dimensional array of beads distinguishable by a combination of fluorescence intensity (five levels) and size (two sizes) is the QuantumPlex™ microspheres (Bangs Laboratories, Fisher, Ind.). An example of a two-dimensional array of doubly-dyed beads distinguishable by the levels of fluorescence of each of the two dyes is described in McDade and Fulton, April 1997, Medical Device & Diagnostic Industry; and Fulton et al., 1997, Clinical Chemistry 43(9):1749-1756.

Each of the microparticle arrays described above has disadvantages that limit their utility. Arrays based on different size microparticles are problematical because the amount of capture reagent that can be bound to a microparticle, which affects the sensitivity and dynamic range of the assay, is dependent on the particle size. Thus, to obtain uniform assay performance for all analytes, it is desirable to use microparticles of uniform size. One-dimensional arrays based on differences in the fluorescent intensity of a single dye typically are limited to about 10 different microparticle populations. Although useful for a wide range of assays, it is desirable to have more distinct microparticle populations to enable the simultaneous detection of greater numbers of analytes. Two-dimensional arrays based on differences in the fluorescence intensities of two distinct dyes enable much larger arrays, but are significantly more difficult to manufacture, and increase the difficulty in subsequent data analysis.

SUMMARY OF THE INVENTION

The present invention relates to multidimensional arrays formed from populations of singly dyed microparticles. The use of singly dyed microparticles to form multidimensional arrays greatly simplifies the creation of multiplex assays, yet still provides most of the advantages arrays formed from multiply dyed microparticles.

Multidimensional arrays of the present invention contain a plurality of sets of microparticle populations, wherein different populations within a set are labeled, using the same fluorophore, at a plurality of discrete fluorescence levels, and populations in different sets are labeled with different fluorophores, wherein the emission of each fluorophore, as measured in the same two detection channels, exhibits distinct relative amounts of emission in the two detection channels. In preferred embodiments, the array contains at least three sets of microparticle populations, more preferably at least four, and more preferably at least five.

The present invention is based on the surprising discovery that by using spectrally similar fluorophores having overlapping emission spectra, practical multidimensional arrays can be created from a plurality of one-dimensional arrays, each based on differences in the fluorescent intensity of a single fluorophore, and that such arrays created from three or more one-dimensional arrays can be analyzed using two detection channels. The overlapping emission spectra of the fluorophores enable the detection of emission from each of the fluorophores using the same two detection channels.

The fluorescence properties of the multidimensional array of the invention enable the identification of the microparticles in each population by exposing the array to excitation light and measuring the fluorescence of each microparticle in each of the two detection channels. The resulting fluorescence data can be plotted in a two-dimensional dot-plot, plotting intensity of the two detection channels on the two axes, as is routinely used in flow cytometry. Each population will appear as cluster uniquely positioned in the two-dimensional dot plot.

The breadth of the emission spectrum of a typical fluorophore is normally regarded as an undesirable property. For example, in flow cytometry, fluorescent dyes are selected where possible such that the emission spectra overlap minimally, and different detector channels are used to detect different dyes. To maximize detection sensitivity, each detector channel is selected such that, as much as possible, it corresponds to the emission maximum of the single dye that it is intended to detect. Emission detected from the other dyes, caused by the breadth of the other dye's emission spectrum, often referred to as "spillover" or "crosstalk", is undesirable and interferes with the independent measurement of dye fluorescence in these previously described methods.

In contrast, the present invention makes use of the breadth of the emission spectrum, and the resulting emission in two detection channels, to distinguish the fluorophores. The emission spectra of different fluorophores having similar emission peaks will overlap each of the two channels to differing degrees and, consequently, will exhibit different relative emission in the two channels. Thus, both microparticle populations labeled with different dyes (i.e., in different sets) and microparticle populations labeled with different amount of the same dye (i.e., in the same set) can distinguished by the different emission intensities in the two detector channels.

The microparticle arrays of the present invention can be used essentially in any application in which multiplex particle arrays are used or are useful, including applications in which the microparticles are used a solid substrates for ligand binding assays or as labeling reagents. A preferred use of the arrays is to implement multiplex binding assays for the simultaneous detection of two or more analytes using, for example, flow cytometry or microscopy. For use in such assays, the microparticles are coated with analyte-specific reagents such that microparticles within a population are coated with reagents having the same known specificity and microparticles in different populations are coated with reagents having different specificities. The identity of the microparticle populations, determined from the microparticle fluorescence measured in the two detection channels, enables identification of the analyte bound to the microparticle through the analyte-specific reagent. One skilled in the art will understand that detection can be carried out using any of a number of different assay formats, including sandwich hybridization formats and competitive assay formats.

Also comprehended by this disclosure are compositions and kits which include a multidimensional array disclosed herein.

DETAILED DESCRIPTION OF THE INVENTION

Figure 1:
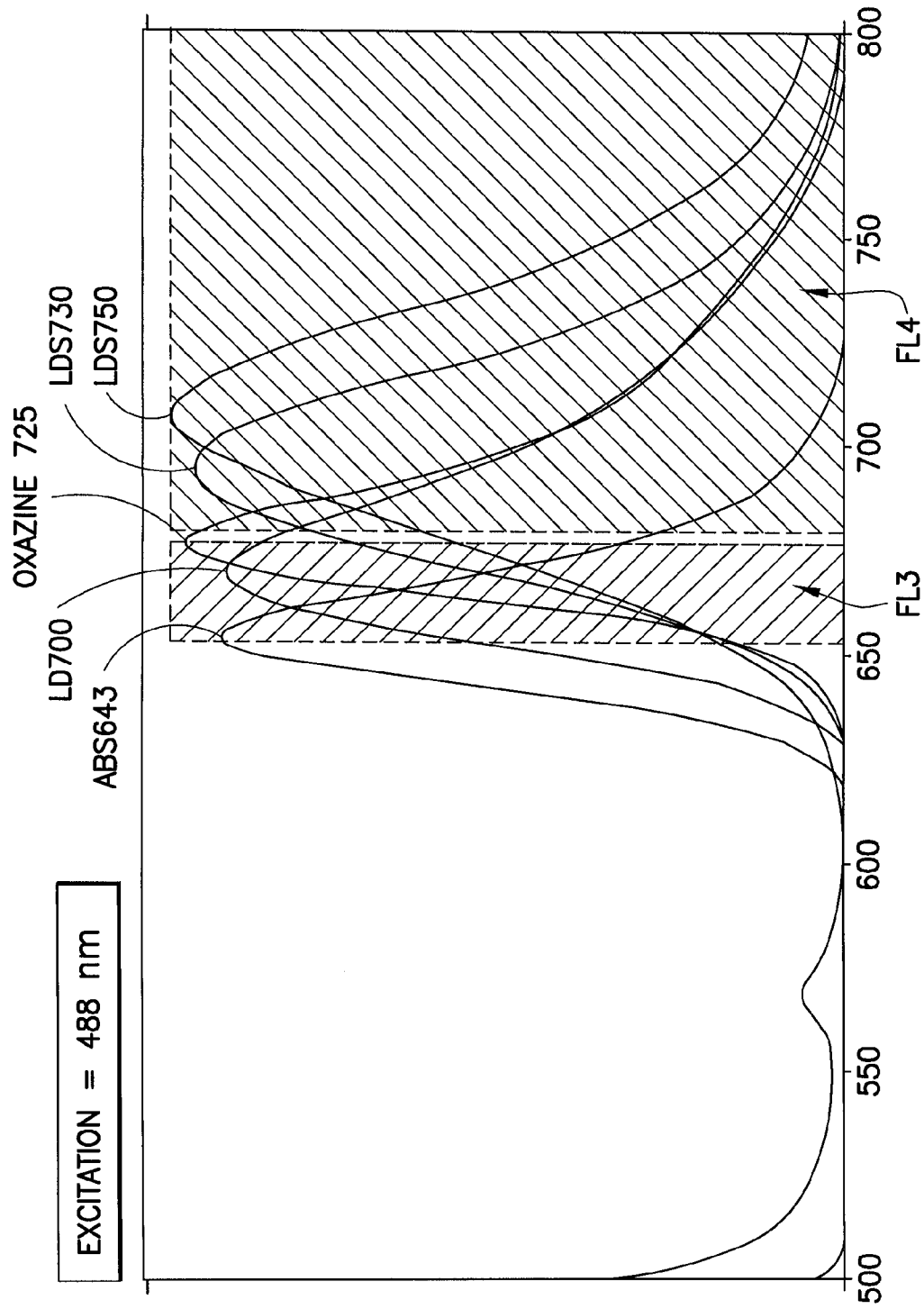
FIG. 1 shows the overlapping emission spectra of multiple dyes, as used in the arrays described in Examples 2 and 3.

The following definitions are provided for clarity. Unless otherwise indicated, all terms are used as is common in the art. All reference cited herein, both supra and infra, are incorporated herein by reference.

As used herein, the terms "microparticles", "microbeads", or "beads" are used interchangeably. These terms refer to small particles with a diameter in the nanometer to micrometer range, typically about 0.01 to 1,000 µm in diameter, preferably about 0.1 to 100 µm, more preferably about 1 to 100 µm, and, for use in flow cytometry, typically about 1 to 10 µm. Microparticles can be of any shape, but typically are approximately spherical ("microspheres").

Microparticles serve as solid supports or substrates to which other materials, such as target-specific reagents, reactants, and labels, can be coupled. Microparticles can be made of any appropriate material (or combinations thereof), including, but not limited to polymers such as polystyrene; polystyrene which contains other co-polymers such as divinylbenzene; polymethylmethacrylate (PMMA); polyvinyltoluene (PVT); copolymers such as styrene/butadiene, styrene/vinyltoluene; latex; or other materials, such as silica (e.g., $SiO_2$).

Microparticles suitable for use in the present invention are well known in the art and commercially available from a number of sources. Unstained microspheres in a variety of sizes and polymer compositions that are suitable for the preparation of fluorescent microparticles of the invention are available from a variety of sources, including: Bangs Laboratories (Carmel, Ind.), Interfacial Dynamics Corporation (Portland, Oreg.), Dynal (Great Neck, N.Y.), Polysciences (Warrington, Pa.), Seradyne (Indianapolis, Ind.), Magsphere (Pasadena, Calif.), Duke Scientific Corporation (Palo Alto, Calif.), Spherotech Inc. (Libertyville, Ill.) and Rhone-Poulenc (Paris, France). Chemical monomers for preparation of microspheres are available from numerous sources.

As used herein, "microparticle population" refers to a group of microparticles that possess essentially the same optical properties with respect to the parameters to be measured, such as synthesized microparticles that, within practical manufacturing tolerances, are of the same size, shape, composition, and are labeled with the same kind and amount of dye molecules. For example, unlabeled microparticles, microparticles labeled with a first dye at a first concentration, microparticles labeled with the first dye at a second concentration, and microparticles beads labeled with a second dye at the third concentration could constitute four distinct bead populations.

The microparticle arrays of the present invention are detected using instruments that have the ability to detect fluorescence light emitted in defined frequency ranges, referred to as "detector channels" or "detection channels". Typically, such instruments contain multiple photodetectors, such as photomultiplier tubes or photodiodes, and the range of wavelengths detected by each photodetector is determined by the use of frequency-dependent filters, dichroic mirrors, or other dispersive elements, as is well known in the art. Alternatively, the same detector can be used for multiple frequency ranges by changing the dispersive elements during analysis, as is typical in fluorescence microscopy.

For identification of microparticles in the arrays of the present invention, two detector channels are used that are close enough that portions of the emission spectrum of each dye falls within each channel. The detector channels can be non-overlapping channels or partially overlapping. The selection of dyes and appropriate corresponding detection channels is well known and within the ability of one of skill in the art.

Choice of the detection channels will depend on the application and the instrumentation used. For example, for use in a flow cytometer in which two channels are used to detect microparticle fluorescence and a third is used to detect reporter fluorescence, it is advantageous to minimize the spillover of the microparticle emissions into the reporter channel. Thus, the channels are selected such that the two channels used for detecting the microparticle emission are spectrally separated from the reporter Is channel, within the constraints imposed by the instrument and dyes available. Again, the selection of compatible dyes and channels is well known and within the ability of one of skill in the art.

The term "analyte" is used herein broadly to refer to any substance to be analyzed, detected, measured, or labeled. Examples of analytes include, but are not limited to: proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants and combinations thereof. It will be understood that detection of, for example, a cell, is typically carried out by detecting a particular component, such as a cell-surface molecule, and that both the component and the bacteria as a whole can be described as the analyte.

As used herein an "analyte-specific reagent" or "target-specific reagent" broadly encompasses any reagent that preferentially binds to an analyte or target of interest, relative to other analytes potentially present in a sample. A target (analyte) and target-specific (analyte-specific) reagent are members of a binding pair, and either member of the pair can be used as the target-specific reagent in order to selectively bind to the other member of the pair. Examples of target and target-specific reagent pairs include, but are not limited to, antigen and antigen-specific antibody; hormone and hormone receptor; hapten and anti-hapten; biotin and avidin or steptavidin; enzyme and enzyme cofactor; and lectin and specific carbohydrate.

Preferred target-specific reagents are antibodies or fragments thereof that include an antigen binding site that specifically binds (immunoreacts with) an antigen.

I. Microparticle Array

The array of present invention is comprised of populations of microparticles, wherein each microparticle is labeled with a single fluorescent dye. The array consists of a plurality of sets of microparticle populations, wherein each set contains a plurality of microparticle populations. Microparticle populations within a set are labeled, using the same fluorophore, such that each population exhibits a measurably distinct mean fluorescence intensity. Microparticle populations in different sets are labeled with different fluorescent dyes, wherein all of the fluorescent dyes can be excited by the same excitation light, the emission spectra of each dye is detectable using the same two detection channels, and the relative amount of emissions in each of the two detection channels is distinguishably distinct between different dyes.

The microparticles in the array are detected and uniquely identified by exposing the microparticles to excitation light and measuring the fluorescence of each microparticle in each of the two detection channels. The excitation light may be from one or more light sources and may be either narrow or broadband. Examples of excitation light sources include lasers, light emitting diodes, and arc lamps. Fluorescence emitted in detection channels used to identify the microparticles may be measured following excitation with a single light source, or may be measured separately following excitation with distinct light sources. If separate excitation light sources are used to excite the microparticle dyes, the dyes preferably are selected such that all the dyes used to construct the array are excitable by each of the excitation light sources used.

For example, a BD FACSCalibur dual laser flow cytometer (BD Bioscience, San Jose, Calif.) has 488 nm and 635 nm excitation lasers that are focused on the flow stream at spatially discrete regions, and detection optics designed to measure light in three detection channels, designated FL1, FL2, and FL3, following excitation by the 488 nm laser, and a fourth detection channel, designated FL4, following excitation by the 635 nm laser. In a preferred embodiment described in the examples, FL3 and FL4 are selected as the two detection channels used to identify the microparticle populations. Thus, in this embodiment, one channel, FL3, is measured following excitation by the 488 nm laser and the second channel, FL4, is measured following excitation by the 635 nm laser. The selection of dyes and detection channels in this example was made in view of the configuration of an existing commercial instrument. Alternatively, a flow cytometer could be configured to measure emission in both FL3 and FL4 following excitation with a single laser.

The resulting fluorescence data from the microparticles preferably is analyzed by plotting the fluorescence intensity values on a two-dimensional dot plot, plotting intensity of the two detection channels on the two axis, as is routinely used in flow cytometry. Each population of microparticles will yield a cluster uniquely positioned in the two-dimensional dot plot. The expected patterns in the dot-plot can be seen from the following analysis.

Let $F_{i1}$ and $F_{i2}$ be the mean fluorescence measurements of a ith dyed population in fluorescence channels 1 and 2, respectively, and $R_i=F_{i2}/F_{i1}$ be the ratio of intensities for the ith population. Because the relative emission in the two channels is a property of the fluorophore's emission spectrum, the ratio of the intensities, for each dye, is a constant. Thus, in a linear×linear dot-plot in which the mean fluorescence intensities in channels 2 and 1 are plotted on the ordinate and abscissa, respectively, microparticle populations dyed with different amounts of the same fluorophore (i.e., populations within the same set) will fall on the line $F_{i2}=R_i \cdot F_{i1}$, wherein the slope is equal to $R_i$, the ratio of emissions in the two channels. Populations in different sets will fall on lines having different slopes (different ratios of emissions in the two channels) and will display in different regions of the dot-plot.

Figure 2:
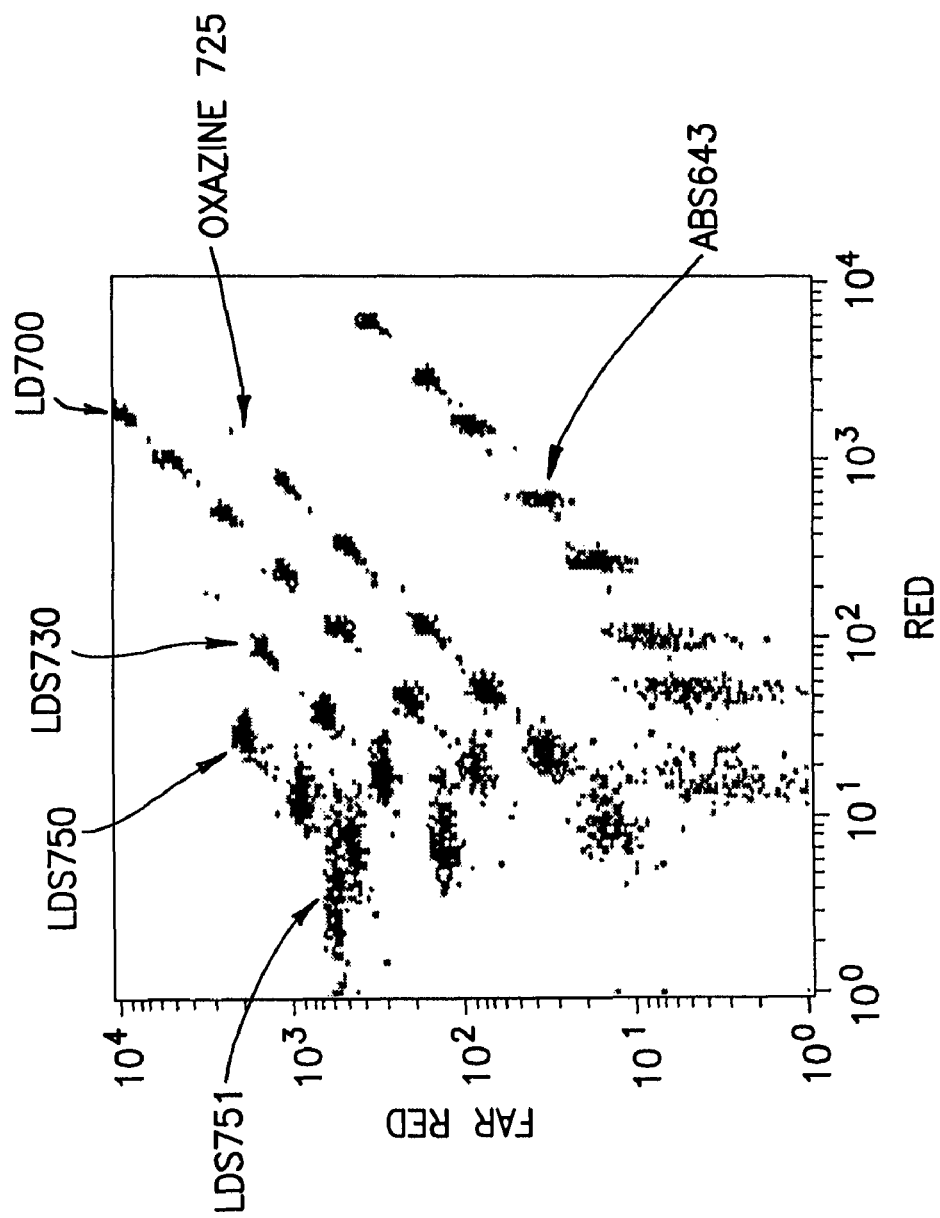
FIG. 2 shows a dot-plot of an array containing 29 distinct populations of beads, as described in Example 2.
Figure 3:
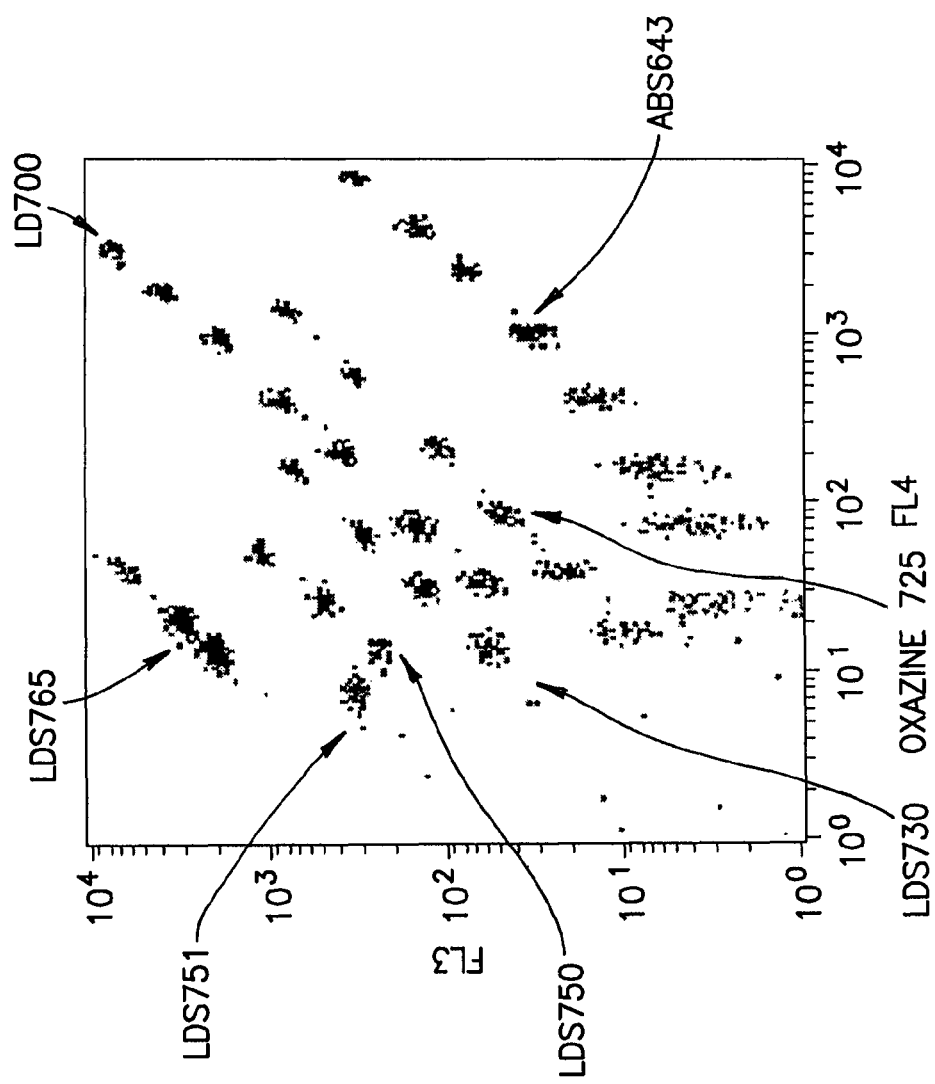
FIG. 3 shows a dot-pot of an array containing 32 distinct populations of beads as described in Example 3.

Flourescent intensity data obtained by flow cytometry typically is plotted using log-transformed data. Using the transformed values, $\log(F_{i2})=\log(R_i)+\log(F_{i1})$. Thus, on a log×log dot-plot, populations in all sets are expected to fall on lines having the same slope, but different "y-intercepts". FIGS. 2 and 3 show data presented on log x log dot-plots.

II. Fluorophores

Fluorescent dyes (fluorophores) suitable for use in the present invention can be selected from any of the many dyes suitable for use in imaging applications (e.g., flow cytometry). A large number of dyes are commercially available from a variety of sources, such as, for example, Molecular Probes (Eugene, Oreg.) and Exciton (Dayton, Ohio), that provide great flexibility in selecting a set of dyes having the desired spectral properties.

Dyes used in the present invention to label microparticle populations in the different sets are selected such that the emission spectra of each dye is detectable using the same two detection channels, and the relative amount of emissions in each of the two detection channels is distinguishably distinct between different dyes. Selection of candidate dyes can be carried out routinely based on the emission spectra of the dyes. Candidate dyes are then evaluated empirically by dyeing microparticle populations using a concentration series of each dye and subsequently analyzing the results. A suitable subset of the dyed microparticles are then selected for use together in a single array.

Depending on the application, the dyes may be selected based on additional criteria. For example, in embodiments in which the microparticles are used in a binding assay wherein an additional reporter fluorophore is used to measure the amount of binding, it is advantageous to minimize the spillover of the microparticle emissions into the channel used to measure the reporter fluorescence. The detection channels are selected such that the two channels used for detecting the microparticle emission are spectrally separated from the reporter channel, and the dyes used are selected to minimize spillover of the microparticle emissions into the reporter channel.

Examples of fluorophores from which a suitable set can be selected include, but are not limited to, 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N, N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio).

It will be clear to one of skill in the art that the suitability of particular dyes or classes of dyes will depend on the method by which the microparticles are labeled, as described further, below. For example, large fluorescent proteins may be suitable for labeling microparticles by binding the dyes to the surface of the microparticle, but likely would not be suitable for internal labeling using bath-dyeing methods. Suitable candidate dyes can be selected routinely based on the labeling methods used.

III. Labeling of Microparticles

Fluorescent dyes have been incorporated into uniform microspheres in a variety of ways, for example by copolymerization of the fluorescent dye into the microspheres during manufacture (U.S. Pat. No. 4,609,689 to Schwartz et al. (1975), U.S. Pat. No. 4,326,008 to Rembaum (1982), both incorporated by reference); by entrapment of the fluorescent dye into the microspheres during the polymerization process; or by non-covalent incorporation of the fluorescent dye into previously prepared microspheres (U.S. Pat. Nos. 5,326,692; 5,723,218; 5,573,909; 5,786,219; and 6,514,295; each incorporated by reference). The method of labeling the microspheres is not a critical aspect of the invention; any method that allows the labeling of the microparticles with a controllable amount of dye can be used.

In a preferred embodiment, the fluorescently labeled microspheres of the invention are prepared by bath dying of microspheres according to well-known methods. Bath dyeing methods are described, for example, in U.S. Pat. Nos. 5,326, 692; 5,723,218; 5,573,909; 5,786,219; and 6,514,295, which describe bath dyeing methods using a plurality of dyes, which are equally applicable to dyeing microparticles with single dyes.

IV. Methods of Use

The microparticle arrays of the present invention can be used essentially in any application in which multiplex microparticle arrays are used or are useful, including application in which the microparticles are used a solid substrates for ligand binding assays or as labeling reagents.

A preferred use of the arrays is to implement multiplex binding assays for the simultaneous detection of two or more analytes using, for example, flow cytometry or microscopy. For use in such assays, the microparticles are coated with analyte-specific reagents such that microparticles within a population are coated with the reagents of the same known specificity and microparticles in different populations are coated with reagents having different specificities. The identity of the microparticle populations, determined from the microparticle fluorescence, enables identification of the analyte bound to the microparticle through the analyte-specific reagent.

Analyte detection assays can be carried out using both competitive and non-competitive formats. Examples of non-competitive assays include sandwich assays in which a second analyte-specific reagent (a reporter) is labeled to facilitate detection of analytes bound to a microparticle. The microparticle array and fluorescently labeled reporter reagents, one for each species of analyte to be detected, are incubated with a sample containing (or suspected of containing) the analytes of interest to allow for the formation of bead-analyte-reporter complexes for each analyte present. The resulting complexes are analyzed, preferably by flow cytometry, to identify and, optionally, quantify the analytes present in the sample. Because the identity of the analyte bound to the complex is indicated by the identity of the bead, multiple analytes can be simultaneously detected using the same fluorophore for all reporter reagents.

In a competitive assay, the sample suspected of containing analyte is incubated with the microparticle array and an analyte-analogue that is capable of competing with the analyte for the limited number of binding sites provided by coated microparticle. In one embodiment, analyte-analogue labeled with a reporter fluorophore is provided in a concentration sufficient to saturate the binding sites on the microparticle. The presence of analyte, which competes with and thereby reduces the number of labeled analyte-analogues bound to the microparticle, results in a measurable decrease in the reporter fluorescence associated with the microparticle.

In an alternative embodiment, microparticle arrays of the present invention are useful as labeling reagents. The microparticles in each population are coated with an target-specific reagent, wherein the target is any molecule to be labeled. The sample is incubated with the array for a time sufficient to allow the target molecules to bind to the target-specific reagent coating the microparticles, thus labeling the molecules. The use of the multidimensional arrays of the invention enables labeling a large number of distinct target molecules while requiring only two detection channels to uniquely identify the labels. In a preferred embodiment, microparticle arrays of the present invention are used as labeling reagents in fluorescence microscopy.

Methods for attaching an antibody or other target-specific reagent to a microparticle are known in the art. Commercially available microparticles typically are provided with amino groups or carboxyl groups to facilitate the covalent attachment of antibodies using well known chemistry. However, any method used by those skilled in the art may be employed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

Preparation a Microparticle Array

This example describes preferred methods for preparing a microparticle array for use in flow cytometry.

The array described herein is intended for use in a detection assay in which the microparticles are coated with an analyte-specific reagent, and a labeled-reporter reagents are used to measure the amount of analyte bound to a microparticle. To maximize sensitivity of the detection assay, it is desirable to label the reporter reagents with a particularly bright fluorophore, preferably phycoerythrin (PE), which has an emission maximum at 578 nm. Thus, the array is prepared assuming that an appropriate detection channel is reserved for measuring the PE-labeled reporter reagents.

1. Detection Channels

The detection channels used to measure the microparticle fluorescence are selected from the channels available using a flow cytometer. Preferred flow cytometers are the BD FACSCalibur™ flow cytometer and the BD FACSArray™ flow cytometer (BD Biosciences, San Jose, Calif.). The filters, which define the detector channels, differ slightly between the two instruments (in the standard, commercially available configurations).

A BD FACSCalibur dual laser flow cytometer has 488 nm and 635 nm excitation lasers. Fluorescence following excitation by the 488 nm laser is measured in the following detection channels:

FL1: 530/30 nm (515-545 nm)
FL2: 585/42 nm (564-606 nm)
FL3: 670 nm Long Pass (>670 nm)

Fluorescence following excitation by the 635 nm laser is measured in the following detection channel:

FL4: 661/16 nm (653-669 nm)

Using a BD FACSCalibur flow cytometer, the FL2 channel is used for measuring the PE-labeled reporter, and microparticle populations are identified from the emissions in the FL3 and FL4 detector channels.

The BD FACSArray flow cytometer has 532 nm and 635 nm excitation lasers. Fluorescence following excitation by the 532 nm laser is measured in the following detection channels:

Yellow: 585/42 nm (564-606 nm)
Far Red: 685 nm long pass (>685 nm)

Fluorescence following excitation by the 635 nm laser is measured in the following detection channels:

NIR (Near Infra Red):780/60 nm (750-810 nm)
Red: 661/16 nm (653-669 nm)

Using a BD FACSArray flow cytometer, the Yellow detection channel is used to measure the PE-labeled reporter reagent, and bead populations are identified from the emissions in the Red and Far Red detector channels.

2. Dyes

Candidate dyes are selected in a routine manner based on their emission spectra such that the all the dyes emit in the two detection channels selected for use in identifying bead populations, as described above. Additionally, the dyes are selected such that the emission of the dyes in the PE-detection channel (FL2 or Yellow) is minimal. Preferred sets of preferred dyes are described in the following examples.

3. Preparation of Microparticles

Suitable undyed microparticles for use in constructing an array are 7.7 micron, 10% solid polymeric beads from Bangs Laboratories (Carmel, Ind.). Prior to dyeing, the beads are prepared as follows. The beads are washed 3 times in 15 ml MeOH. The beads are then washed in 15 ml of anhydrous MeOH (MgSO$_4$-treated) and then suspended in 17.5 ml of anhydrous MeOH. For dyeing, 1 ml portions (3.86×10⁷ beads) are put into separate tubes, each containing a small stirring bar, and stirred.

4. Preparation of Dyeing Solutions

For each dye, a series of 1.0 ml dyeing solutions are prepared consisting of the dyeing reagents in the proportions shown in the table, below.

| Tube | 30% MeOH/70% EtOH | 1,4 Dioxane | Dye (0.1 μmole/μl in DMF) |
|---|---|---|---|
| A | 500 μl | 420 μl | 80 μl |
| B | 540 μl | 420 μl | 40 μl |
| C | 560 μl | 420 μl | 20 μl |
| D | 570 μl | 420 μl | 10 μl |
| E | 575 μl | 420 μl | 5 μl |
| F | 577.5 μl | 420 μl | 2.5 μl |
| G | 578.75 μl | 420 μl | 1.25 μl |
| H | 579.4 μl | 420 μl | 0.6 μl |

Alternatively, another suitable organic solvent, such as $CH_2Cl_2$, can be used in place of 1,4 Dioxane.

5. Bead Dyeing

Each of the 1 ml dyeing solutions is added to a separate tube containing a 1 ml preparation of washed beads while stirring vigorously at room temperature. The bead/dye mixtures are stirred at 50° C. for 1 hour in the dark to allow the dye to be absorbed into the beads.

After dyeing, 10 ml of MeOH are added to each tube. The tubes are vortexed and then centrifuged at ~3,000 rpm for 4 minutes to pellet the dyed beads. The pellets are washed 2 times with 5 ml MeOH, then washed with 10 ml of 0.05% Tween-20, 0.1% $NaN_3$, then suspended in 3 ml of 0.05% Tween-20, 0.1% $NaN_3$. The concentration of the resulting dyed bead solution is approximately $10^4$/μl ($10^7$/ml).

6. Testing and Selection of Bead Populations

Dyeing is carried out as described above using each of the candidate dyes to generate a plurality of bead sets, each set dyed with a different candidate dye, and each set containing a series of bead populations dyed with different concentrations of the same dye. The plurality of bead sets represents a candidate array from which a suitable array is selected. The selection of a suitable array is determined empirically, and will depend on a number of parameters, such as the dyes selected and the dyeing efficiencies.

To select an suitable array from the candidate array, bead populations are analyzed on either a BD FACSCalibur™ flow cytometer or a BD FACSArray™ flow cytometer using the detector channels described above, and the fluorescence intensity data from each bead in each of the two detector channels are plotted in a two-dimensional dot-plot. Bead populations that form well-defined clusters that are simultaneously on-scale (i.e., the data not compressed against an edge of the dot-plot) and essentially not overlapping with other bead populations are selected for use in the combined array.

Additionally, the emission from the beads is measured in the PE-channel (FL2 or Yellow) to determine the amount of spillover into the channel used to measure the PE-labeled reporter molecules. Preferably, the spillover into the PE-channel is minimal so as to minimize interference in the measurement of the reporter reagents.

Because the selection of bead populations to use in the array is empirical, bead dyeing and analysis is expected to be an iterative process in which beads are incrementally added to an existing array. Appropriate adjustments can be made to the dyeing procedure in a routine manner based on the experimental results. For example, if most populations within an initially dyed set are off scale because the dye intensity is too high, such that only a subset was selected for use in the final array, additional populations of beads can be dyed using a lower concentration of dye. Subsequent analysis with the first dyed populations selected for inclusion in the array will allow for extending the size of the array. Furthermore, an additional set of bead populations, dyed with a distinct dye, can be added incrementally to an existing set to extend the size of the array.

Example 2

29-Population Array

Bead subsets were prepared essentially as described in Example 1 using each of the dyes listed in the table, below. All dyes were obtained from Exciton (Dayton, Ohio). Excitation and emission maxima, which were measured in either ethanol, methanol, or dichloromethane, are known to be somewhat dependent on the solvent used for the measurements, and slightly different results may be obtained using different solvents.

| Dye | Excitation Max | Emission Max | Populations used in array |
|---|---|---|---|
| LD700 | 647 | 673 | 7 |
| LDS730 | 614 | 695 | 4 |
| LDS750 | 572 | 704 | 3 |
| LDS751 | 542 | 700 | 1 |
| Oxazine 725 | 645 | 676 | 6 |
| ABS643 | 640 | 655 | 8 |

The emission spectra of these dyes (with the exception of LDS751) are shown in FIG. 1. Also shown are the boundaries of the detection channel defined using a BD FACSArray flow cytometer.

Sets of dyed beads, each containing bead populations dyed with different amounts of one of the dyes, were combined and were analyzed on a BD FACSArray flow cytometer, as described above. Bead populations that were both uniquely distinguishable and simultaneously on-scale in a Far Red× Red dot-plot were selected empirically for use in the final multiplex bead set. FIG. 2 shows a dot-plot (Far Red×Red) of the selected bead array containing 29 distinguishable bead populations. The number of bead populations used in the final set from each of the subsets is indicated in the table, above.

The emissions of the bead populations in the PE-channel (Yellow) also were measured (results not shown), and minimal spillover was observed for all populations.

Example 3

Extended Array

The bead array described in Example 2 was incrementally extended by the inclusion of a bead set dyed using LDS765 (Exciton, Dayton, Ohio), prepared essentially as described above. The measured excitation and emission maxima for the dye are shown in the table, below:

| Dye | Excitation Max | Emission Max | Populations used in array |
|---|---|---|---|
| LD765 | 595 | 752 | 3 |

For this analysis, the sets of dyed beads, were analyzed on a BD FACSCalibur flow cytometer, as described above. Bead populations from the set dyed with LDS765 were selected such that the populations were both uniquely distinguishable and simultaneously on-scale relative to the bead populations in the previously constructed array. Three populations could be added to the 29-population array. FIG. 3 shows a dot-plot (FL3×FL4) of the selected bead array containing 32 distinguishable bead populations.

The emissions of the bead populations in the PE-channel (FL2) also were measured (results not shown), and minimal spillover was observed for all populations.

We claim:

1. A method of measuring a plurality of analytes in a sample comprising:
   a) contacting a sample with an array of populations of microparticles, comprising
   i) a plurality of sets,
      wherein each set contains a plurality of populations of microparticles,
      wherein microparticle populations within a set are labeled with different levels of a single fluorophore such that each population exhibits a measurably distinct fluorescence intensity;
   wherein microparticles in different sets are labeled with different fluorophores; wherein all of said fluorophores have overlapping emission spectra and emit light that is detectable using a single pair of detection channels, and the relative emission in each of the two detection channels is distinguishably distinct between different fluorophores;
   wherein each of said microparticle populations is distinguishable by its fluorescence emissions in said pair of detection channels; and
   wherein said array comprises at least 3 sets of microparticle populations; and
   ii) a plurality of analyte-specific reagents,
      wherein reagents of the same specificity are coupled to microparticles in the same population, and reagents of different specificity are coupled to microparticles in different populations;
   for a time sufficient to allow for the formation of microparticle-analyte complexes;
   b) exposing said microparticle-analyte complexes to excitation light;
   c) measuring fluorescence of each of said microparticle-analyte complexes in each of said pair of detector channels;
   d) identifying the specificity of said analyte-specific reagents coupled to said microparticles, thereby identifying the analyte present in each of said microparticle-analyte complexes;
   e) measuring the amount of analyte present in each of said microparticle-analyte complexes, to provide a measure of the plurality of analytes present in said sample.

2. The method of claim 1, wherein said sample is further contacted with a set of fluorescently labeled analyte-specific reporter reagents, wherein said set contains an analyte-specific reporter reagent specific for each analyte to be measured.

3. The method of claim 1, wherein said detecting is carried out by flow cytometry.

4. The method of claim 1, wherein at least one of said analyte-specific reagents is an antibody that binds specifically to an analyte that is an antigen, or at least one of said analyte-specific reactants is an antigen that binds specifically to an analyte that is an antibody.

5. The method of claim 1, wherein said array comprises at least 4 sets of microparticle populations.

6. The method of claim 1, wherein said array comprises at least 5 sets of microparticle populations.

7. The method of claim 1, wherein said array comprises at least 20 populations of microparticles.

8. The method of claim 1, wherein said array comprises at least 30 populations of microparticles.

* * * * *